US008288363B2

(12) United States Patent
Bourgougnon et al.

(10) Patent No.: US 8,288,363 B2
(45) Date of Patent: Oct. 16, 2012

(54) MEDICAMENTS FOR ANTI-HERPES VIRUS TREATMENTS

(75) Inventors: Nathalie Bourgougnon, Saint-Ave (FR); Jean-Claude Yvin, Saint-Malo (FR)

(73) Assignee: ASE & BIO, Paris (FR)

( * ) Notice: Subject to any disclaimer, the term of this patent is extended or adjusted under 35 U.S.C. 154(b) by 656 days.

(21) Appl. No.: 12/299,365

(22) PCT Filed: May 3, 2007

(86) PCT No.: PCT/FR2007/000761
§ 371 (c)(1),
(2), (4) Date: Nov. 3, 2008

(87) PCT Pub. No.: WO2007/128914
PCT Pub. Date: Nov. 15, 2007

(65) Prior Publication Data
US 2009/0176733 A1 Jul. 9, 2009

(30) Foreign Application Priority Data

May 4, 2006 (FR) ..................................... 06 03990

(51) Int. Cl.
*A61K 31/70* (2006.01)
(52) U.S. Cl. .......................................... 514/54
(58) Field of Classification Search ................ 514/54
See application file for complete search history.

(56) References Cited

U.S. PATENT DOCUMENTS 5,874,479 A * 2/1999 Martin ........................... 514/724
6,337,324 B1 * 1/2002 Harmenberg et al. ......... 514/171

FOREIGN PATENT DOCUMENTS
WO WO 95/24907 A2 9/1995

OTHER PUBLICATIONS

Baba M., et al., (1988) "Sulfated polysaccharides are potent and selective inhibitors of various enveloped viruses including herpes simplex virus cytomegalovirus vesicular stomatitis virus and human immunodeficiency virus" Antimicrobial Agents and Chemotherapy, vol. 32, No. 11, pp. 1742-1745.
Hashimoto K., et al., (1996) "Antiviral activity of a sulphated polysaccharide extracted from the marine Pseudomonas and marine plant Dinoflagellata against human immunodeficiency viruses and other enveloped viruses" Antiviral Chemistry and Chemotherapy, vol. 7, No. 4m pp. 189-196.
Koizumi N., et al., (1993) "Anti-HIV (Human Immunodeficiency Virus) Activity of sulfated paramylon" Antiviral Research, vol. 1, No. 21, pp. 1-14.
Katsuraya K., et al., (1994) "Synthesis of sulfated alkyl malto- and laminara-oligosaccharides with potent inhibitory effects of AIDS virus infection" Carbohydrate Research, vol. 260, No. 1, pp. 51-61.
Shieh M.T., et al., (1992) "Cell surface receptors for herpes simplex virus are heparan sulfate proteoglycans" The Journal of Cell Biology, vol. 116, No. 5, pp. 1273-1281.
Menard Rozenn, et al., (2004) "beta-1,3 glucan sulfate, but not beta-1.3 glucan, induces teh salicylic acid signaling pathway in tobacco and Arabidopsis" Plant Cell, vol. 16, No. 11, pp. 3020-3032.
Kelly et al., "Kinetic Effects of Inorganic Pyrophosphate Analogs on Several Inorganic Pyrophosphate Hydrolyzing Enzymes," Biochemistry, vol. 12, No. 17, 1973.
Zakirova et al., "The Effect of Pyrophosphate Analogues on the Activity of the Inorganic Pyrophosphatase from *Escherichia coli*," Engelhardt Institute of Molecular Biology, Russian Academy of Sciences at Vavilova 32, GSP Moscow, 119991 Russia, Nov. 22, 2001.

* cited by examiner

*Primary Examiner* — Elli Peselev
(74) *Attorney, Agent, or Firm* — McDonnell Boehnen Hulbert & Berghoff LLP (57) ABSTRACT

Disclosed are compositions comprising and methods of using sulphated or phoshated polysaccharides for the treatment of diseases caused by herpes viruses, more particularly by alpha-herpes viruses, and in particular by HSV-1 and HSV-2, as well as by strains of these viruses which are resistant to known antiviral agents.

14 Claims, 6 Drawing Sheets

MEDICAMENTS FOR ANTI-HERPES VIRUS TREATMENTS

The invention relates to novel medicaments for treatments against herpes viruses (Herpesviridae).

It is known that herpes viruses belong to a virus family the genome of which is composed of double-stranded linear DNA coding encoding 100 to 200 genes and is encapsulated in an icosahedral protein cage called the capsid, which is itself wrapped in a lipid membrane called the envelope.

The herpes virus family comprises three sub-families, that is to say the alpha-herpes viruses, the beta-herpes viruses and the gamma-herpes viruses.

The alpha-herpes viruses are characterized by a tropism with respect to a large number of cell types. Among the alpha viruses there may be mentioned the herpes simplex virus 1 (HSV-1) and the herpes simplex virus 2 (HSV-2), which are responsible for buccal and/or genital herpes, and the varicella-zoster virus (VZV) responsible for varicella and zoster.

The beta-herpes viruses are characterized by a tropism with respect to a restricted number of cell types. The cytomegalovirus (CMV) responsible for a mononucleosis syndrome and the human herpes viruses type 6 (HHV6) and type 7 (HHV7) responsible for roseola, belong to this sub-family.

The gamma-herpes viruses are characterized by a tropism limited to lymphocytes. Among the viruses of this sub-family there may be mentioned the Epstein-Barr virus (EBV) responsible for infectious mononucleosis, Burkitt's lymphoma and nasopharyngeal carcinoma, and the Kaposi's sarcoma-associated herpes virus or rhadinovirus (KSHV) responsible for lymphoma.

Herpes infection comprises a primary infection phase and latency phases interrupted by reactivation phases. During the primary infection or initial infection the virus penetrates into epithelial cells, where it multiplies and produces a cell lysis at the inoculation site. The virus can then make use of the sensitive nerve pathway to advance to the nuclei of the ganglion neurons. While the primary infection is often accompanied by a short period of clinical illness, the long-term latency is asymptomatic. During the latency phases the intracellular virus does not replicate. The virus remains in the nucleus of the nerve ganglion neurons in the form of extrachromosomal DNA, without integrating the cell genome. The choice of neurons as the latency site allows the viruses to escape the immune system. Following certain stimuli, such as ultraviolet radiation, fever or emotional stress, the virus may reactivate and commence transcription of numerous genes which lead to accelerated replication. Clinically, the reactivation is often accompanied by the appearance of non-specific symptoms, such as mild fever, a state of fatigue, erythema, as well as clinical symptoms, such as swollen or painful lymphatic ganglions, and immunological symptoms, such as a reduction in the number of natural killer cells.

One of the particularities of the herpes virus lies in its capacity for remaining present in a host cell in a latent form without producing viral particles throughout the life of the host, and in its capacity for reactivation, which may give rise to multiple infections.

The penetration of the herpes virus into the host cell constitutes an essential stage of the infection. It starts by adsorption of the virus on to the cell surface by the intermediary of specific receptors and non-specific receptors with respect to receptors included in the cell membrane. After the adsorption process, the virus penetrates into the cell by fusion of the viral envelope with the cell membrane, thus releasing the nucleocapsid into the cytoplasm. The nucleocapsid is then degraded by enzymatic proteolysis resulting in the release of the viral DNA, which migrates towards the nucleus of the host cell and penetrates into the latter.

Once it has arrived inside the nucleus, the viral DNA is transcribed into viral mRNA by the cell RNA polymerase II. The expression of viral genes is called "ordered", which reflects the fact that it comprises several successive phases, that is to say a so-called "immediate early" phase, a so-called "early" phase and a so-called "late" phase.

During the immediate early phase, immediate early viral proteins (immediate early antigens) are expressed. These are regulator proteins which attach themselves to the cell DNA and cause a stop to the synthesis of certain cell proteins, while causing an increase in the synthesis of other proteins.

During the early phase, the viral enzymatic proteins, such as DNA polymerase and thymidine kinase, are expressed. These two enzymes are very important for replication of the virus. Mutations of these enzymes are responsible for resistance to anti-herpes agents.

Finally, during the late phase it is late viral proteins (late antigens) which correspond, inter alia, to structural proteins of the capsid and tegument which are expressed.

Assembling of the nucleocapsid of viruses newly formed by replication takes place in several stages which remain poorly defined.

The mature virus becomes infectious during its sprouting at the nuclear membrane. The viruses newly formed by replication are released outside the cell either by lysis of the cell membrane or by the formation of a vacuole. The duration of the replication cycle is approximately 18 to 20 hours. The efficiency of the replication manifests itself by the fact that one infectious viral particle is synthesized per 100 to 1,000 viruses produced in the host cell.

Treatments currently used to combat herpes viruses, in particular HSV-1 and HSV-2, are aimed at blocking their replication cycle.

In these treatments two groups of antiviral agents are used, suitable for inhibiting the synthesis of the DNA of the herpes viruses, these being on the one hand nucleoside inhibitors and on the other hand non-nucleoside inhibitors of the viral DNA polymerase.

Among the nucleoside inhibitors of the viral DNA polymerase there may be mentioned acyclovir, penciclovir and their respective prodrugs, that is to say valacyclovir and famciclovir. The nucleoside inhibitors are distinguished from the natural nucleosides by modifications to their sugar or to their purine or pyrimidine base. They enter into competition with natural nucleosides and prevent elongation of the DNA chain.

Acyclovir is the preferred nucleoside inhibitor for treatment of herpes infections. In order to be able to act against the virus, it must first be phosphorylated by the viral enzyme thymidine kinase (TK); it must then be subjected to other phosphorylations realized by cell enzymes, which allows it to arrive at its active form. In this active form, acyclovir is a very selective inhibitor of the viral DNA polymerase, which it inhibits more than the cell DNA polymerase.

As regards non-nucleoside inhibitors, these are analogues of inorganic pyrophosphate. These molecules do not have to be phosphorylated beforehand in order to inhibit the viral enzymes. Treatments based on non-nucleoside inhibitors are used in the case of infections resistant to nucleoside analogues. Among the non-nucleoside inhibitors of viral DNA polymerase there may be mentioned foscarnet.

The limits of the treatments used to combat herpes viruses, in particular HSV-1 and HSV-2, are currently due to the toxicity of the inhibitors used, the emergence of resistant viral strains and the fact that these treatments are only active on the viruses during the replication phase.

The resistance mechanism of certain viral strains to acyclovir is mainly due to the presence of mutations on the gene coding for the viral TK, which induces an alteration in its function. Thus, a deficient TK will no longer be able to phosphorylate acyclovir. However, a mutant viral strain containing a deficient TK is no less viable, since the enzyme TK is not essential for replication of the virus.

In immunocompetent individuals, the appearance of HSV strains resistant to acyclovir is very rare, but has been indicated. In contrast, this risk is higher in the case of immunodeficient individuals, that is to say those undergoing an immunodepressive therapy, which is the case in particular for persons who have undergone an organ transplant, those suffering from acquired immunodeficiency syndrome (AIDS) or those who have major changes to the skin, such as major burns.

Several factors are said to be associated with this resistance phenomenon encountered in immunodeficient individuals. Firstly, there is heterogeneity of the viral populations present in an infected individual. Certain mutant strains are said to be produced from minority viral sub-populations naturally resistant to a given antiviral agent (thus, approximately 0.01% of HSV viruses are spontaneously resistant to acyclovir or ACV). There is also the fact that the degree of immunodeficiency of an infected individual would seem to play an important role in influencing the immunity factors involved in the limitation of viral replication. Finally, prolonged use of antiviral agents at sometimes sub-optimum doses may promote the development of viral resistance (Englund et al., Ann. Intern. Med., 1990, 112: 416-22).

As already indicated above, foscarnet is currently the only anti-herpes virus agent approved for treatment of infections caused by HSV resistant to nucleoside analogues. However, long-term treatment with foscarnet frequently involves a high intolerance Finally, there is currently no anti-herpes vaccine allowing preventive treatment.

In view of the above considerations, it has become necessary to direct research efforts to other therapy targets and to develop novel antiviral agents which allow herpes infection to be combated.

It has been found that such a promising therapy target is located at the entry of the viral particles into the cell, and more particularly at the adsorption mechanism of these viral particles on the cell surface; a particular benefit of this target is that it is located upstream of the penetration of the nucleocapsids into the cells, in other words the viral replication.

The adsorption is a critical stage of the infection.

It is already known that certain sulphated polysaccharides, in particular dextran sulphate, are capable of interfering in the adsorption mechanism of certain enveloped viruses, in particular HSV-1 and HSV-2 (Baba et al., Antimicrobial Agents and Chemotherapy, 1988, 32: 1742-1745).

Thus, Mazumder et al. (Inter. J. Biol. Macromol, 2002, 31: 87-95) have demonstrated that a polysaccharide of very high molecular weight (165,197 Da), an extract of a red alga *Gracilaria corticata*, exerted an inhibitory effect with respect to the adsorption of HSV-1 and HSV-2 viruses on vero cells.

Furthermore, Yingzhou et al. (China J. I., 2004, 6: 23) have demonstrated that a polysaccharide extracted from another species of red alga, *Eucheuma striatum* also had an inhibitory effect on the adsorption of the HSV-1 virus on cells in vitro.

However, these works have not led to the development of novel treatments against herpes viruses.

The purpose of the invention is therefore, in particular, to provide the medical profession with novel medicaments of high therapeutic index for combating herpes viruses in general, and more particularly alpha-herpes viruses, and in particular HSV-1 and HSV-2, these medicaments essentially opposing multiplication of said viruses by inhibition of the adsorption of the latter on the host cell.

It is to the credit of the applicant company to have found, surprisingly and unexpectedly, that it was possible to achieve this object by the use of particular polysaccharides.

The present invention thus first relates to the use, for the preparation of a medicament intended for treatment of diseases caused by herpes viruses, more particularly by alpha-herpes viruses, and in particular by HSV-1 and HSV-2, as well as by strains of these viruses which are resistant to the antiviral agents already known, of at least one polysaccharide of formula (I)

wherein
$R^1$ represents either a hydrogen atom, a sulphate group or a phosphate group, or a sulphated or phosphated glucose bonded to the saccharide structure, preferably by a bond of the $\beta(1\rightarrow 6)$ type,
$R^2$ represents a hydrogen atom, a sulphate group or a phosphate group, $R^1$ and $R^2$ not being able to represent a hydrogen atom simultaneously,
X and Y each independently represent an OH group, a glucose, a sulphated or phosphated glucose, a mannitol or a sulphated or phosphated mannitol,
n represents an integer from 11 to 30, preferably from 20 to 30, more preferably from 25 to 30,
said polysaccharide having a degree of sulphation greater than 2, preferably from 2.2 to 2.4, or a degree of phosphation greater than 1, preferably from 1.5 to 2.5, said medicament acting in particular by inhibition of the adsorption of the viruses in question on the host cell.

In a particular embodiment, the polysaccharide used is a polysaccharide of formula (I) wherein $R^1$ and $R^2$ can be either identical and then represent a sulphate or phosphate group, or different from one another, $R^1$ then representing a sulphated or phosphated glucose unit bonded to the saccharide structure, preferably by a β bond of the β-1,6 type, X and/or Y representing a mannitol group and n representing an integer from 11 to 30, more particularly from 25 to 30, said medicament acting in particular by inhibition of the adsorption of the viruses in question on the host cell.

The applicant has furthermore demonstrated, surprisingly and unexpectedly, that the medicament produced using a polysaccharide of formula (I) according to the invention acts by inhibition of the adsorption of the viruses in question on the host cell. Moreover, the applicant has also been able to demonstrate that the polysaccharides of formula (I) according to the invention, and in particular sulphated laminarin, had no toxicity in vitro and in vivo, nor any anti-anticoagulant activity and therefore no risks of secondary haemorrhagic effects, and had a high therapeutic index.

In the context of the invention, by "therapeutic index" or "TI" is meant the ratio between the maximum non-toxic dose (or a dose inducing a quantified toxicity) and the dose inducing a favourable pharmacological effect.

In the context of the present invention, by "degree of sulphation" is meant the average number of sulphated OH groups per saccharide unit. A degree of sulphation greater than 2 indicates that over the entire polysaccharide, on average more than 2 OH groups per saccharide unit are sulphated.

In the context of the present invention, by "degree of phosphation" is meant the average number of phosphated OH groups per saccharide unit. A degree of phosphation greater than 1 indicates that over the entire polysaccharide, on average more than 1 OH group per saccharide unit is phosphated.

In the context of the invention, by "sulphate group" is meant a group of the ($-SO_3H$) type.

In the context of the invention, by "phosphate group" is meant a group of the ($-PO_3H_2$) type.

Another subject of the present invention is the use, for the implementation of a method for treatment of diseases caused by herpes viruses, more particularly by alpha-herpes viruses, and in particular by HSV-1 and HSV-2, as well as by strains of these viruses which are resistant to the antiviral agents already known, of at least one polysaccharide of formula (I) as defined above.

According to an advantageous embodiment, said polysaccharide of formula (I) is a sulphated laminarin having a degree of sulphation greater than 2, and preferably from 2.2 to 2.4. Preferably, the sulphated laminarin used according to the invention has a degree of polymerization of 11 to 28.

According to another advantageous embodiment, said polysaccharide of formula (I) is a laminarin phosphate having a degree of phosphation greater than 1, and preferably from 1.5 to 2.5. Preferably, the laminarin phosphate used according to the invention has a degree of polymerization of 11 to 28.

Preferably, the polysaccharide of formula (I) is a sulphated laminarin having a degree of sulphation equal to approximately 2.3 and a degree of polymerization of 11 to 28, called "laminarin PS3".

In the context of the invention, by "degree of polymerization" is meant the number of monosaccharide units bonded to one another by bonds of the $\beta(1\rightarrow3)$ type making up the main linear chain. A degree of polymerization of 11 to 28 indicates a polysaccharide composed of 11 to 28 saccharide unit, in particular glucose, bonded to one another by bonds of the $\beta(\rightarrow3)$ type. This degree of polymerization does not take into account glucose units bonded by $\beta(1\rightarrow6)$ to the main polysaccharide chain. The degree of polymerization is therefore equal to n+2 if X and Y simultaneously represent OH, to n+3 if only one of X or Y represents OH and to n+4 if neither X nor Y represents OH.

Astonishingly and surprisingly, the applicant has been able to demonstrate that the sulphated laminarin having a degree of sulphation greater than 2, preferably from 2.2 to 2.4, and a degree of polymerization of 11 to 28 was particularly effective for treatment of diseases caused by herpes viruses, preferably chosen from those caused by alpha-herpes viruses, and in particular by HSV-1 and HSV-2, as well as by strains of these viruses which are resistant to the antiviral agents already known. This sulphated laminarin also has a low anticoagulant activity, without risks of secondary haemorrhagic effects, thus confirming its great benefit for the production of a medicament intended for administration to humans or animals, and also has a high therapeutic index.

According to another advantageous embodiment, the invention provides the use of an oligosaccharide obtained from the sulphated laminarin having a degree of sulphation greater than 2, and preferably from 2.2 to 2.4, the degree of polymerization of this oligosaccharide being from 11 to 28, for the preparation of a medicament for treatments against herpes viruses in general, more particularly against the alpha-herpes viruses, and in particular against HSV-1 and HSV-2, this medicament, which is also active against strains resistant to the antiviral agents already known, acting on the multiplication of said viruses, in particular by inhibition of the adsorption of the latter on the host cell.

According to another advantageous embodiment, the invention provides the use of an oligosaccharide obtained from the laminarin phosphate having a degree of phosphation greater than 1, and preferably from 1.5 to 2.5, the degree of polymerization of this oligosaccharide being from 11 to 28, for the preparation of a medicament for treatments against herpes viruses in general, more particularly against the alpha-herpes viruses, and in particular against HSV-1 and HSV-2, this medicament, which is also active against strains resistant to the antiviral agents already known, acting on the multiplication of said viruses, in particular by inhibition of the adsorption of the latter on the host cell.

A particular embodiment of the invention relates to the use of a sulphated laminarin, characterized in that it has a degree of sulphation greater than 2, preferably from 2.2 to 2.4, and a degree of polymerization of 11 to 28, for the production of a medicament intended for treatment of diseases caused by herpes viruses.

Another particular embodiment of the invention relates to the use of a sulphated laminarin, characterized in that it has a degree of sulphation greater than 2, preferably from 2.2 to 2.4, and a degree of polymerization of 11 to 28, for the implementation of a method for treatment of diseases caused by herpes viruses.

Another particular embodiment of the invention relates to the use of a laminarin phosphate, characterized in that it has a degree of phosphation greater than 1, preferably from 1.5 to 2.5, and a degree of polymerization of 11 to 28, for the production of a medicament intended for treatment of diseases caused by herpes viruses.

Another particular embodiment of the invention relates to the use of a laminarin phosphate, characterized in that it has a degree of phosphation greater than 1, preferably from 1.5 to 2.5, and a degree of polymerization of 11 to 28, for the implementation of a method for treatment of diseases caused by herpes viruses.

According to a preferred embodiment of the invention, the diseases caused by herpes viruses are preferably chosen from those of immunodeficient individuals, more particularly from those of individuals who have received transplants, individuals suffering from acquired immunodeficiency syndrome or individuals who have major changes to the skin, and in particular major burns.

In particular, in the context of the invention by "disease caused by herpes viruses" is meant in particular buccal herpes, genital herpes, varicella, zoster, infectious mononucleosis, Burkitt's lymphoma, nasopharyngeal carcinoma, mononucleosis syndrome, retinitis, roseola, Kaposi's sarcoma or also all the lymphomas associated with herpes viruses.

Furthermore, in the context of the invention by "herpes viruses" or "Herpesviridae" is meant human and animal herpes viruses belonging in particular to families of Alphaherpesvirinae, Betaherpesvirinae and Gammaherpesvirinae. More particularly, the invention relates to viruses of the simplex virus, varicellovirus, mardivirus, iltovirus, cytomegalovirus, muromegalovirus, roseolovirus, lymphocryptovirus and rhadinovirus type, and also ictaluviruses. Preferably, in the context of the invention by herpes viruses is meant the viruses HSV-1, HSV-2, VZV (varicella zoster virus), HHV-4 or EBV (Epstein-Barr virus), HHV-5 or CMV, HHV-7, and HHV-8 or KSHV.

According to an advantageous embodiment, the invention provides the use of a polysaccharide of formula I, more particularly of the sulphated laminarin having a degree of sulphation greater than 2, and preferably from 2.2 to 2.4, for the preparation of a medicament for treatments against alpha-herpes viruses, and in particular against HSV-1 and HSV-2, quite particularly intended for immunodeficient individuals, more particularly for individuals who have received transplants, individuals suffering from acquired immunodeficiency syndrome (AIDS) or individuals who have major changes to the skin, and in particular major burns.

The invention also relates to a pharmaceutical composition comprising as active ingredient an effective amount of at least one polysaccharide of formula I as defined above, and more particularly sulphated laminarin having a degree of sulphation greater than 2, and preferably from 2.2 to 2.4, as well as an effective amount of at least one compound chosen from the group consisting of nucleoside inhibitors and non-nucleoside inhibitors of a viral enzyme of a herpes virus.

In the context of the invention, by "nucleoside inhibitors" is meant, in particular and without being limited thereto, acyclovir, penciclovir, cidofovir, ganciclovir, valganciclovir, valacyclovir and famciclovir.

In the context of the invention, by "non-nucleoside inhibitors" is meant in particular analogues of inorganic pyrophosphate, in particular foscarnet.

In such a pharmaceutical composition, the polysaccharide of formula (I) and the compound chosen from the group consisting of nucleoside inhibitors and non-nucleoside inhibitors of a viral enzyme of a herpes virus can be used simultaneously, separately or spread over time.

Indeed, a person skilled in the art is able to define the most suitable administration which allows the best therapeutic index to be obtained for the patient. Each active ingredient can be administered sequentially, even by different routes, or at the same time.

In the context of the invention, by "effective amount" is meant an amount of active ingredient sufficient to obtain a therapeutic effect on a patient.

The present invention also relates to a method for treatment of diseases caused by herpes viruses, more particularly by alpha-herpes viruses, and in particular by HSV-1 and HSV-2, as well as by strains of these viruses which are resistant to the antiviral agents already known, comprising the administration of an effective amount of a medicament comprising as active agent at least one polysaccharide of formula (I) as defined above to a patient suffering from said disease caused by herpes viruses.

In the context of the present invention, by "patient" is meant any warm-blooded animal, in particular mammals, and especially human beings.

In a particular embodiment, the polysaccharide of formula (I) used in the treatment method according to the invention is a sulphated laminarin, characterized in that it has a degree of sulphation greater than 2, preferably from 2.2 to 2.4, and a degree of polymerization of 11 to 28.

In another embodiment of the invention, the polysaccharide of formula (I) used in the treatment method is a laminarin phosphate, characterized in that it has a degree of phosphation greater than 1, preferably from 1.5 to 2.5, and a degree of polymerization of 11 to 28.

In an advantageous embodiment, the treatment method as defined above comprises, in addition to the administration of at least one polysaccharide of formula (I) as defined above, simultaneous or sequential administration of an effective amount of at least one compound chosen from the group consisting of nucleoside inhibitors and non-nucleoside inhibitors of a viral enzyme of a herpes virus.

In a particular embodiment, the treatment method according to the invention is characterized in that said patients suffering from a disease caused by herpes viruses are chosen from immunodeficient individuals, more particularly from individuals who have received transplants, individuals suffering from acquired immunodeficiency syndrome or individuals who have major changes to the skin, and in particular major burns.

For the preparation of a sulphated polysaccharide of formula (I) in the context of the invention, a sulphation stage is carried out, preferably in accordance with the protocol described by Alban S, Kraus J, and Franz G in "Synthesis of laminarin sulfates with anticoagulant activity", Arzneim. Forsch./Drug Res. (1992) 42; 1005-1008. This process has been perfected in the thesis of Susanne Alban, defended in 1993 at the University of Regensburg and bearing the title "Synthese und physiologische Testung neuartiger Heparinoide [Synthesis and Physiological Testing of Novel Heparinoids]". These processes are suitable for the sulphation of polysaccharides of formula (I) of the invention and allow a highly substituted sulphated polysaccharide to be obtained without degradation and with a good reproducibility in a simple and not particularly involved manner.

To obtain an effective sulphation of the polysaccharide without degradation of the polysaccharide chains, the sulphation reaction is advantageously carried out under conditions corresponding to an absolute absence of water. Before the sulphation, the polysaccharide is therefore preferably dried, for example over phosphorus pentoxide ($P_2O_5$), and then dissolved in dimethylformamide, or DMF. On the basis of its alternative effects on the polysaccharide, DMF has an activating influence by substitution. In fact, the combination of polar DMF with the OH groups least to the cleavage of the intra- and intermolecular hydrogen bonds and to the disintegration of superior structures.

The complex $SO_3$-pyridine can advantageously be used to carry out the sulphation reaction.

As a result of the coordination of the electron acceptor $SO_3$ with the electron donor pyridine, the reactivity of $SO_3$, which is difficult to control and manifests itself in highly exothermic reactions resulting in degradations, is reduced. The complex $SO_3$-pyridine has the advantage over other complexes of being neither too reactive nor too stable, that is to say too slow from the point of view of reaction.

Because of the fact that the degree of sulphation obtained is proportional to the molar excess of sulphation reagent and given that a degree of substitution greater than 2 is sought, a concentration of 6 moles of $SO_3$-pyridine per mole of glucose is advantageously used.

To guarantee the absence of water, the reaction can advantageously be carried out under an argon atmosphere.

Preferably, from the start of the reaction the pyridine is added to the sulphation reagent in an equimolar amount in order to directly trap the sulphuric acid which could form by reaction of the complex $SO_3$-pyridine with water. The concentration of the polysaccharide and that of the sulphation reagent must preferably be as high as possible, the solubility of the polysaccharide and of the sulphation reagent limiting the final degree of sulphation. In order to avoid cooling of the mixture at the start of the reaction, which could result in solubility problems, and in order to obtain the most regular substitution possible, the solution of the complex $SO_3$-pyridine in DMF could be added not all at once but continuously over a period of 4 hours.

The sulphation reaction can be carried out at a temperature of 20 to 60° C., preferably approximately 40° C. Higher temperatures result in a more efficient substitution, but also a degradation of the chains.

After the addition of the sulphation reagent, the mixture is preferably stirred for several hours at approximately 60° C. At this temperature an additional substitution takes place, without degradation of the chains.

The supernatant of the mixture is then advantageously separated off by decanting. The residue is dissolved, preferably in NaOH, and the solution is then mixed with 10 times its volume of ethanol. The precipitate which forms at a temperature of 4-8° C. overnight is isolated and then preferably dissolved in dilute soda (solution of approximately pH 9). The solution is dialyzed in order to remove the salts and the molecules of low molecular weight and is then advantageously brought to pH 7.0 by addition of NaOH, and thereafter is lyophilized The resulting sulphated polysaccharide is in the form of sodium salt.

The degree of sulphation is preferably determined by conductometric titration of the free acid of the sulphated polysaccharide, or alternatively by ion chromatography after hydrolysis using a system of the HPLC type. The first method has the advantage of also being suitable for investigations relating to the stability (the consumption of soda increases as the sulphate groups are removed), whereas the HPLC method requires less substance and can be automated. As a control, it is possible to determine the sulphur content by elemental analysis.

It is furthermore possible to control the homogeneity of the sulphation and the distribution of sulphate groups over the various positions in the glucose molecule by a modified form of methylation analysis followed by GC-MS analysis (that is to say gas chromatography, mass spectrometry).

The degree of sulphation obtained by proceeding as indicated above is greater than 2, more precisely from 2 to 2.5, and quite particularly from 2.2 to 2.4.

According to an advantageous embodiment, the polysaccharide of formula (I), and preferably the sulphated laminarin, are used for the preparation of a medicament for treatment of diseases caused by herpes viruses intended for administration by a general route, and preferably by the oral, rectal, pulmonary, topical (including the transdermal, buccal and sublingual routes) and parenteral routes (including the subcutaneous, intramuscular, intravenous, intradermal and intravitreal routes).

The daily dose is generally from 0.01 to 250 mg per kilo of weight of the patient, and preferably from 0.10 to 100 mg, still more preferably from 0.5 to 30 mg, and quite particularly from 1.0 to 2.0 mg.

These daily doses apply in particular in the case of the sulphated laminarin; for the other salts and esters according to formula (I), the daily doses are adapted to each case.

The daily dose can be administered by a unit dose one, two, three, four, five or six or more times at various times of the day.

The unit doses can contain from 10 to 1,000 mg, from 50 to 400 mg, and preferably from 5 to 100 mg of active ingredient.

The medicaments obtained, in accordance with the invention, using at least one of the polysaccharides of formula (I) contain the conventional formulation ingredients, and possibly one or more other therapeutic agents.

Furthermore, as mentioned above, the polysaccharide of the invention can be advantageously combined with other active ingredient. Their method of administration can be simultaneous or sequential. They can also be administered by various routes as described above.

BRIEF DESCRIPTION OF THE DRAWING

The present invention will be better understood by reading the following non-limiting examples.

EXAMPLE 1

Preparation of a Laminarin Sulphate PS3

Laminarin was first extracted from a raw material made up of brown algae in accordance with the protocol described in the patent FR 92 08387.

When the laminarin had been extracted, a sulphation was carried out in accordance with the protocol described by Alban S, Kraus J, and Franz G in Synthesis of laminarin sulfates with anticoagulant activity, Arzneim. Forsch./Drug Res. (1992) 42; 1005-1008, perfected by the thesis of Susanne Alban, defended in 1993 at the University of Regensburg and bearing the title "Synthese und physiologische Testung neuartiger Heparinoide [Synthesis and Physiological Testing of Novel Heparinoids]".

The laminarin was first dried over phosphorus pentoxide ($P_2O_5$) and then dissolved in dimethylformamide, or DMF.

To carry out the sulphation reaction, the complex $SO_3$-pyridine was then used under an argon atmosphere: the $SO_2$-pyridine in DMF in an equimolar amount was added in one operation but continuously over a period of 4 hours. The sulphation reaction was carried out at a temperature of 40° C. After the addition of the sulphation reagent, stirring of the mixture was continued for 6 hours at 60° C.

The supernatant of the mixture was then separated off by decanting, the residue was dissolved in 2.5 M NaOH and the solution was then mixed with 10 times its volume of 99% ethanol. The solution obtained was then kept at a temperature of 4-8° C. overnight and a precipitate was obtained, which was isolated and then dissolved in dilute soda (solution of approximately pH 9). The solution was then dialyzed using a Spectrapor membrane having a cut-off threshold at 1,000 Da and then brought to pH 7.0 by addition of NaOH. Finally, the solution dialyzed in this way was lyophilized. A laminarin sulphate in the form of the sodium salt was obtained.

The degree of sulphation was then determined by conductometric titration of the free acid of the sulphated polysaccharide using 0.1 N soda. The degree of sulphation of the laminarin obtained was 2.3. The degree of polymerization of the laminarin sulphate obtained in this way was from 23 to 28.

This sulphated polysaccharide was called "sulphated laminarin PS3", or also "PS3".

EXAMPLE 2

Preparation of Cells and Viral Strains

To carry out the various tests described below, vero cells, which are green monkey kidney fibroblast cells (Cercopithecus aethiops, ATCC: CCL 81), were used. These cells have a growth level of 1:20 in 7 days when they are seeded at a concentration of $3 \times 10^5$ cells/ml in an MEM culture medium supplemented with foetal calf serum.

The following viral strains were furthermore used:
a the wild-type strain 17 of HSV-1 ACVs and PFAs
the strain HSV-2,
the acyclovir-resistant strain HSV-1R,
the acyclovir-resistant strain HSV-2R.

These viral strains were supplied by Professor Ingrand (Laboratoire de virologie de Reims, France). To obtain a viral stock for each of these strains, the procedure was as follows:

Vero cells were cultured in a flask to confluence (350,000 cells/ml) in 5 ml of Eagle's minimal essential medium (MEM) supplemented with 8% of foetal calf serum (FSC) containing 500 μl of viral suspension.

The culture flask was then placed in an oven at 37° C. for 2 h. After this incubation the cells were rinsed and then covered again with MEM medium containing 8% FCS.

After 3 to 4 cycles of viral multiplication, corresponding to approximately 3 days of culture, the flask was subjected to 2 successive cycles of freezing and thawing in order to break down the cells and release the intracellular virions.

The culture supernatant was subsequently recovered and then centrifuged for 10 minutes at 600 g using a Jouan MR22i centrifuge such that the cell debris was removed.

The culture supernatant was then frozen at 80° C., this constituting the viral stock. This viral stock was subsequently titrated and then distributed into cryotubes in aliquots of 2 ml and kept at −80° C.

The infectious titre, which corresponds to the number of viral particles per unit volume capable of infecting permissive cells, was determined for each viral strain.

This titration was carried out in accordance with the following protocol in 96-well microtitre plates. Each microtitre plate is composed of 8 lines of 12 wells consequently forming 12 columns of 8 wells. Each line corresponds to a dilution of the stock viral suspension from $10^{-1}$ to $10^{-8}$.

The vero cells were seeded at a cell density of $3.5 \cdot 10^4$ cells/well in 100 μl of MEM medium containing 8% FCS:
one of the columns, called the negative control column, was filled with 50 μl of MEM medium with 8% FCS,
another column, called the positive control column, was filled with 50 μl of culture supernatant originating from the viral stock,
finally, the other ten columns were filled successively with 50 μl of viral supernatant diluted from 10 to 10 in MEM medium containing 8% FCS.

The microtitre plate was then placed in an oven at 37° C. for 72 hours. Four to five multiplication cycles of the virus take place during this period. After 72 hours, the supernatant was removed and the cytopathic effect of the HSV virus was investigated. This cytopathic effect was visualized on the one hand by a swelling and a rounding of the cell nuclei, which assumed a globular appearance, and on the other hand by an organization of the infected cells into chains.

The titre of each viral strain was then determined by the method of Reed and Muench (Am, J. Hyg., 1983, 27: 493-497). According to this titration method, the number of wells exhibiting a cytopathic effect and the number of wells not exhibiting a cytopathic effect are counted for each viral dilution. The range of dilutions used was chosen to be wide enough to include on the one hand the dilution for which all the responses are positive and, on the other hand, the dilution for which all the responses are negative.

The infectious titre was thus expressed in $ID_{50}$/ml, which designates the dose which infects 50% of the cells of the culture under consideration. This titre was calculated according to a statistical formula, after determination of the dilutions enclosing the 50% infection point:

$$\log ID_{50} = \log 10^{-(dilution\ greater\ than\ 50\% + d)} + d$$

where $$d = \frac{(\%\ dilution\ greater\ than\ 50\% - 50\%)}{(\%\ dilution\ greater\ than\ 50\% - dilution\ less\ than\ 50\%)}$$

From this calculation, what is called the multiplicity of infection MOI was determined as a function of the number of cells.

By way of example, the 50% infectious dose of the viral strain HSV-1 is $10^{4.75}$ $ID_{50}$ for 50 μl, that is to say a titre of $2 \times 10^{5.75}$ $ID_{50}$ for 1 ml according to the method of Reed and Muench.

In parallel with this method, the infectious titre of the stock suspension of each viral strain was also determined by measurement of the viability of infected cells by staining with neutral red.

This method is based on the principle that living cells absorb neutral red, which is a vital stain. The optical density of the medium was measured at the maximum absorption wavelength of neutral red, that is to say 540 nm, using a spectrophotometer (SpectraCount™, microplate photometer, Packard). The optical density at 540 nm is proportional to the number of living cells in an infected culture (McLaren et al., Antiviral Research, 1983; 3: 223-234 and Langlois et al., Standardization, 1986, 14: 201-211).

Figure 1:
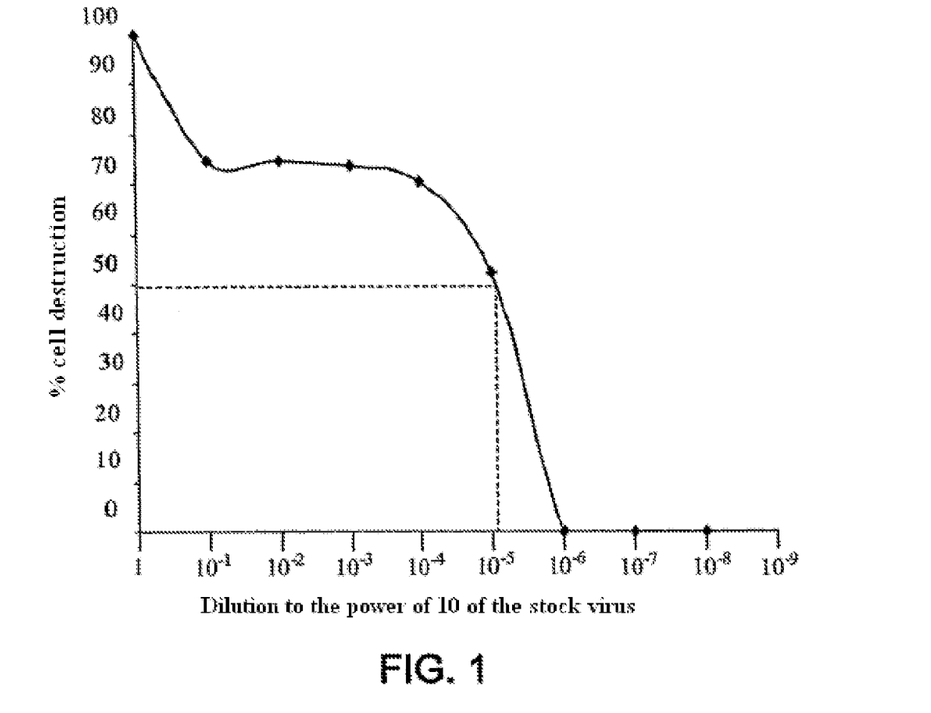
FIG. 1 shows the curve of the titration of a stock suspension of an HSV-1 strain: the percentages of vero cells destroyed are expressed as a function of the viral dilutions of the stock suspension (from 10–1 to 10–8).

The titration curve of the viral strain HSV-1 obtained by the cell viability method with neutral red is shown in FIG. 1. The 50% infectious dose of the viral strain HSV-1 is $10^{5.05}$ per 50 µl, which corresponds to an infectious titre of $2 \times 10^{6.05}$ per 1 ml; the value of $2 \times 10^{6.05}$ is the mean of 4 titrations carried out for the strain HSV-1.

The same protocol enabled the viral titre of each stock suspension to be determined:
- $2 \times 10^{6.05}$ $ID_{50}$/ml for HSV-1
- $2 \times 10^{4.42}$ $ID_{50}$/ml for HSV-1R
- $2 \times 10^{5.31}$ $ID_{50}$/ml for HSV-2
- $2 \times 10^{4.44}$ $ID_{50}$/ml for HSV-2R It was then desired to demonstrate the antiviral activity of the sulphated laminarin PS3 on several viral strains by evaluation of the viability of vero cells infected in the presence of the sulphated laminarin PS3, said antiviral activity manifesting itself by inhibition of the adsorption of the viral strains in question on the host cell.

The effective concentration (EC 50%), that is to say the concentration of the sulphated polysaccharide which enables infection of 50% of the cells of a culture to be inhibited, was measured for each viral strain.

It was thus possible to demonstrate the action mechanism of the sulphated laminarin PS3 by determining its effect on the viral adsorption. The sulphated laminarin PS3 was used either before, during or after infection of the vero cells by various viral strains, or continuously.

By way of comparison, the same experiments were carried out using three comparison products, that is to say dextran sulphate, acyclovir and phycarine, which is the non-sulphated form of the laminarin extracted in Example 1.

EXAMPLE 3

Measurement of the Anti-HSV-1 Activity of the Sulphated Laminarin PS3

In a first series of experiments, the cell viability method was used to determine the anti-herpes activity of the viral strain HSV-1, the infectious viral titre of which is $2 \times 10^{6.05}$ $ID_{50}$/ml.

This anti-herpes activity was evaluated by determining the effective concentrations ($EC_{50}$) of PS3 which enable 50% of the cells of a culture to be protected against infection by viral suspensions of HSV-1 having various MOIs as a function of the incubation time of PS3 (48, 72, 96 and 120 hours).

Acyclovir was used as the comparison product.

The concentration ranges of PS3 used for a given MOI were determined, that is to say
- a the concentration range of PS3 used varies from 12.5 to 1,250 µg/ml for a viral suspension of HSV-1 having an MOI of 1 $ID_{50}$/cell,
- the concentration range of PS3 used varies from 1.25 to 125 µg/ml for a viral suspension of HSV-1 having an MOI of 0.1 $ID_{50}$/cell,
- the concentration range of PS3 used varies from 0.5 to 125 µg/ml for a viral suspension of HSV-1 having an MOI of 0.01 $ID_{50}$/cell, The determination of the $EC_{50}$ was carried out in 96-well microtitre plates in accordance with the following protocol. Vero cells are seeded at a cell density of $3.5 \cdot 10^4$ cells/well in 100 µl of MEM medium containing 8% FCS. For each viral suspension defined by its MOI:
- the negative control column was filled with 100 µl of MEM medium with 8% FCS,
- the virus control column was filled with 50 µl of viral suspension having the required MOI and with 50 µl of MEM medium with 8% FCS,
- the PS3 control column was filled with 50 µl of PS3 having the desired concentration range or with 50 µl of acyclovir (Zovirax 0.05-5 µg/ml
- finally, all the other columns were filled successively with 50 µl of PS3 having the required concentration range or with 50 µl of acyclovir (Zovirax 0.05-5 µg/ml) and with 50 µl of the viral suspension having the desired MOI.

The cells were then incubated in an oven at 37° C. for 48, 72, 96 and 120 hours and the viability of the cells in each well was evaluated after staining with neutral red, in accordance with the method described above.

The $EC_{50}$ corresponding to the concentration which enables the cytopathic effect of the virus to be reduced by 50% was calculated in accordance with the following formula:

$$\frac{OD_{(cells+virus+PS3 \text{ or } acyclovir)} - OD_{(virus \text{ control})}}{OD_{(cells+PS3 \text{ or } acyclovir)} - OD_{(virus \text{ control})}}$$

Figure 2:
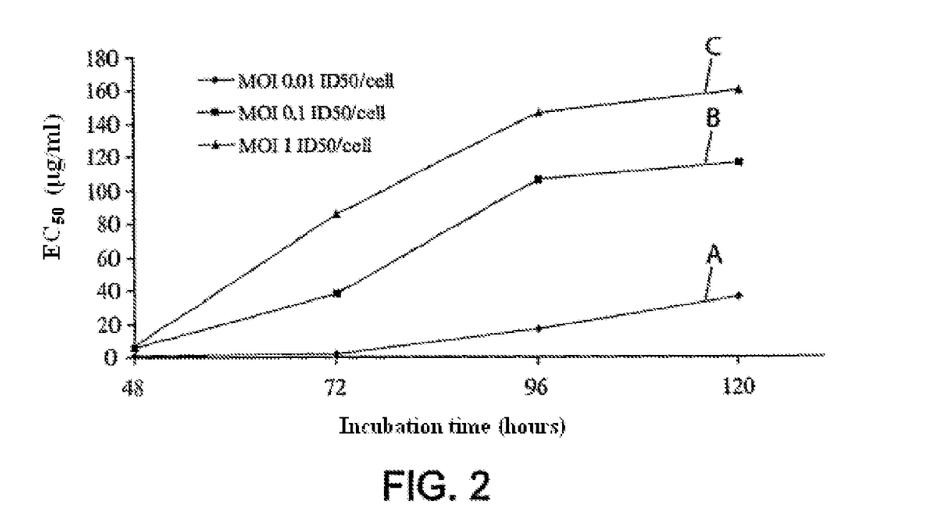
FIG. 2 shows the course of the $EC_{50}$ value of PS3 (µg/ml) in the case of vero cells infected by viral suspensions of HSV-1 having various MOIs (MOI 0.01 $ID_{50}$/cell, curve A, MOI 0.1 $ID_{50}$/cell, curve B and MOI 1 $ID_{50}$/cell, curve C) as a function of the PS3 incubation time (expressed in hours h).

FIG. 2 summarizes the anti-herpes kinetic activity of PS3 for the three different MOIs. For each incubation time it is for the MOI of 0.01 $ID_{50}$/cell that the lowest $EC_{50}$ values were recorded and, conversely, it is for the MOI of 1 $ID_{50}$/cell that the highest $EC_{50}$ values were recorded.

EXAMPLE 4

Comparison Measurement of the Antiviral Activity of the Sulphated Laminarin PS3 on the Strains HSV-1, HSV-1R, HSV-2 and HSV-2R The anti-herpes activity of PS3 was evaluated and compared on each viral suspension of HSV-1, HSV-1R, HSV-2 and HSV-2R defined by an MOI of 0.01 $ID_{50}$/cell for a cell concentration of 350,000 cells/ml, after incubation times of 48 and 72 hours.

Figure 3:
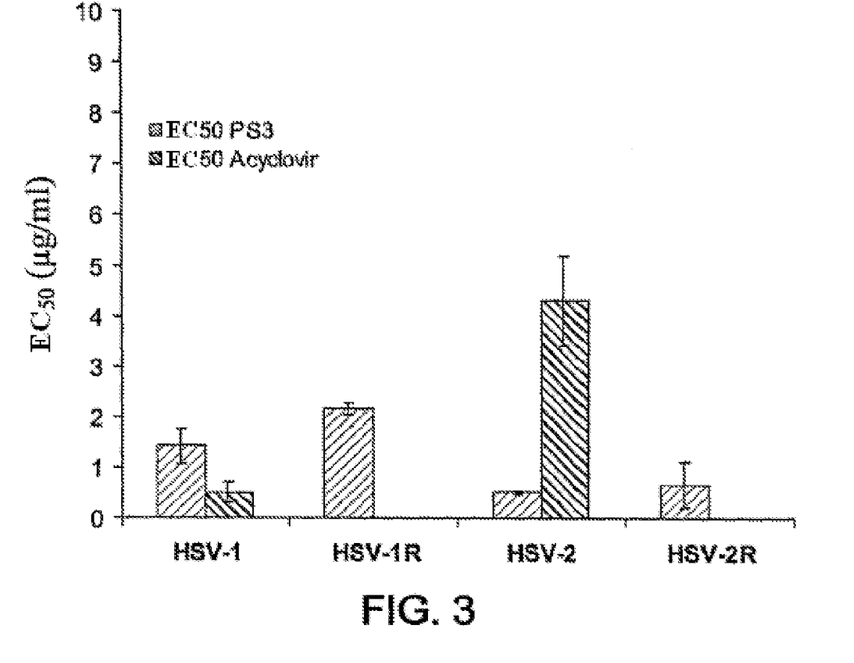
FIG. 3 is a diagram showing the $EC_{50}$ values of PS3 and acyclovir for each of the viral strains studied, HSV-1, HSV-1R, HSV-2 and HSV-2R, after treatment of the infected vero cells for 48 hours.
Figure 4:
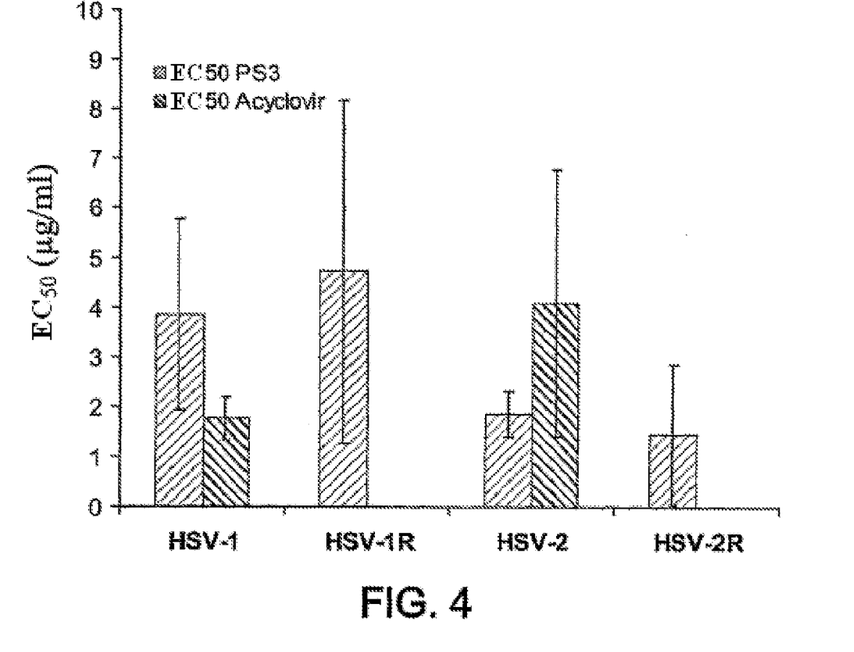
FIG. 4 is a diagram showing the $EC_{50}$ values of PS3 and acyclovir for each of the viral strains studied, HSV-1, HSV-1 R, HSV-2 and HSV-2R, after treatment of the infected vero cells for 72 hours.

This series of experiments was carried out applying the protocol enabling the $EC_{50}$ to be determined, as described in Example 3. FIGS. 3 and 4 allow comparison of the $EC_{50}$ of PS3 on the various strains for incubation times of 48 and 72 hours respectively, the comparison product being acyclovir.

Examination of these figures leads to the conclusion that PS3 is more effective than acyclovir in protecting the vero cells against the strains HSV-1R, HSV-2 and HSV-2R, that is to say against viral strains resistant to acyclovir.

In fact, the $EC_{50}$ value of PS3 is lower than that of acyclovir for each of these strains, regardless of the treatment time.

EXAMPLE 5

Measurement of the Cytotoxic Activity of the Sulphated Laminarin PS3

To determine whether PS3 has a cytotoxic activity, the procedure was as follows. Vero cells were seeded in each well at a cell density of $3.5 \cdot 10^5$ cells/ml in 100 µl of MEM medium containing 8% FCS. The cells were treated with 50 µl of PS3, the concentration of which varies from 0.125 to 2,500 µg/ml, or with 50 µl of acyclovir at a concentration of 5; 1; 0.5; 0.1 and 0.05 µg/ml. 50 µl of MEM medium containing 8% FCS was added to each well. The wells containing untreated cells were filled with 100 μl of MEM medium containing 8% FCS. The cells were then incubated in an oven at 37° C. for 48, 72 and 96 hours.

The cytotoxic activity of PS3 was determined by measurement of the 50% cytotoxic concentration or $CC_{50}$. The $CC_{50}$ corresponds to the concentration of PS3 which inhibits the growth of 50% of the cells of a culture. The $CC_{50}$ value, expressed in percentage cell destruction, was measured by the cell viability method after staining with neutral red, in accordance with the method described above, according to the formula:

$$\frac{Optical\ density_{(untreated\ cells)} - Optical\ density_{(treated\ cells)}}{Optical\ density_{(untreated\ cells)}} \times 100$$

Figure 5:
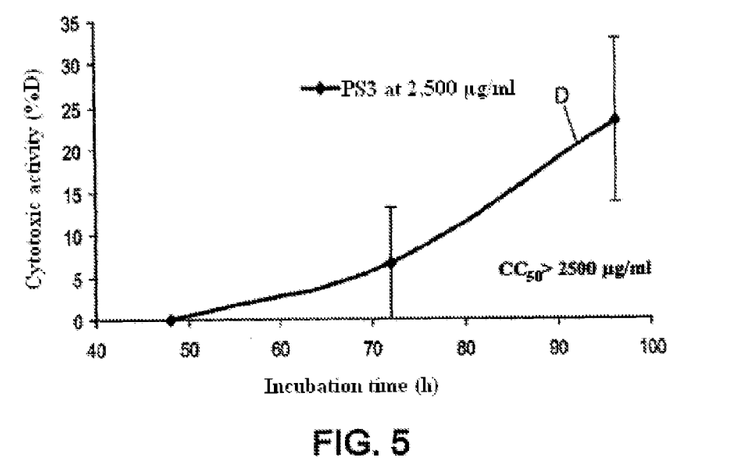
FIG. 5 is a graph showing a curve D of the cytotoxic activity of PS3, the cell destruction percentages ($CC_{50}$) being expressed as a function of the PS3 incubation time (hours h).

FIG. 5 illustrates the percentage cell destruction ($CC_{50}$) for the highest concentration of PS3, that is to say 2,500 μg/ml, as a function of the incubation time (48, 72 and 96 hours). Examination of FIG. 5 reveals that PS3 has no toxic effect for the vero cells, regardless of the incubation time.

EXAMPLE 6

Measurement of the Therapeutic Index of the Sulphated Laminarin PS3, Acyclovir, Dextran Sulphate and Phycarine The therapeutic indices (TI) of PS3, as well as three other reference products, that is to say acyclovir, dextran sulphate and phycarine, were determined in parallel for each viral strain. The TI values are summarized in Table 1 below.

TABLE 1

| Incubation | | Therapeutic index | | | |
|---|---|---|---|---|---|
| time | Substances | HSV-1 | HSV-1R | HSV-2 | HSV-2R |
| 48 hours | PS3 | >1,761 | >1,157 | >4,808 | >3,788 |
| | Acyclovir | >4,902 | 0 | >579 | 0 |
| | Dextran sulphate | — | — | — | — |
| | Phycarine | — | — | — | — |
| 72 hours | PS3 | >651 | >530 | >1,344 | >1,712 |
| | Acyclovir | >1,492 | 0 | >613 | 0 |
| | Dextran sulphate | >868 | >641 | >3,571 | >4,545 |
| | Phycarine | 0 | 0 | 0 | 0 |

— value not determined

The therapeutic index (TI) represents the ratio between the maximum non-toxic dose (or a dose inducing a quantified toxicity) and the dose inducing a favourable pharmacological effect.

Table 1 shows the TI values of PS3, acyclovir, dextran sulphate and phycarine obtained for each of the four vital strains after incubation times of 48 and 72 hours.

Examination of the values shown in Table I lead to the conclusion
 that PS3 is as effective as dextran sulphate on all the strains studied for identical concentrations (0.125-1,250 μg/ml),
 that acyclovir is not effective on the strains HSV-1R and HSV-2R, unlike PS3, and
 that phycarine, which corresponds to the non-sulphated form of PS3, has no anti-herpes activity.

In view on the one hand of the results shown by FIGS. 3 and 4 and on the other hand of those shown in Table I, it seems that PS3 is effective on all the viral strains studied, with $EC_{50}$ values of less than 2 μg/ml after 48 hours of treatment and less than 5 μg/ml after 72 hours of treatment.

It is particularly interesting to note that PS3 is effective on the strains resistant to acyclovir, which is the inhibitor currently used in patients suffering from herpes.

EXAMPLE 7

Determination of the Action Mechanism of the Sulphated Laminarin PS3

A series of experiments was carried out in order to determine the action mechanism of PS3, each stage of the replication cycle of the virus constituting a potential therapy target for combating the virus.

The abovementioned viral suspensions of HSV-1, HSV-1R, HSV-2 and HSV-2R, defined by an MOI of 0.01 $ID_{50}$/cell for a cell concentration of 350,000 cells/ml, were tested.
Action of PS3 on the Viral Infection Acyclovir and dextran sulphate used at concentrations comprised between 0.05 and 5 μg/ml were used as reference products in this series of experiments. PS3 concentrations of 0.125 to 1,250 μg/ml were used, and the experiments were carried out in 96-well microtitre plates.

To verify whether PS3 protects a cell culture when it is used before its infection by the abovementioned viral strains, the procedure was as follows.

Vero cells were seeded at a cell density of 3.5·10 cells/well in 100 μl of MEM medium containing 8% FCS.

A solution of 50 μl of PS3 or the comparison product, that is to say acyclovir having a given concentration, was then added to each well filled with 50 μl of MEM medium with 8% FCS.

The microtitre plate containing the cells treated with PS3 or the reference product was than placed in an oven at 37° C. for 6, 12 or 24 hours. The cells were then washed with 100 μl of MEM medium in order to remove the PS3 or the reference product.

A volume of 50 μl of a viral suspension was then added to each well, as well as 50 μl of MEM medium with 8% FCS; and the plates were kept at 4° C. for 1 hour.

The infected cells were then placed in an oven at 37° C. for 48 or 72 hours.

The viability of the cells in each well was evaluated by staining with neutral red, in accordance with the method described above.

In view of the results obtained, it was possible to conclude that cells pretreated with PS3 or acyclovir before infection were not protected against any of the strains studied.

PS3 therefore does not protect the cells from the viral infection.
Virucidal Action of PS3

To determine whether PS3 has a virucidal effect, the procedure was as follows.

Vero cells were seeded at a cell density of 3·10⁴ cells/well of a microtitre plate in 100 μl of MEM medium containing 8% FCS for 24 hours before the test.

On the day of the test, 50 μl of each of the viral suspensions identified above were treated with 50 μl of PS3 or reference product (acyclovir) having a given concentration for one hour at 37° C.

An amount of 100 μl of the mixture of this viral suspension, to which PS3 or the reference product had been added, was introduced into each well of the microtitre plate. The plate was kept at 4° C. for one hour.

It is to be noted that controls of the growth of the cells and of the viruses were run simultaneously.

The plates containing the infected cells were then placed in an oven at 37° C. for 48 or 72 hours.

The virucidal effect of PS3 was evaluated by measurement of the $EC_{50}$ values determined in accordance with the method described in Example 3.

Figure 6:
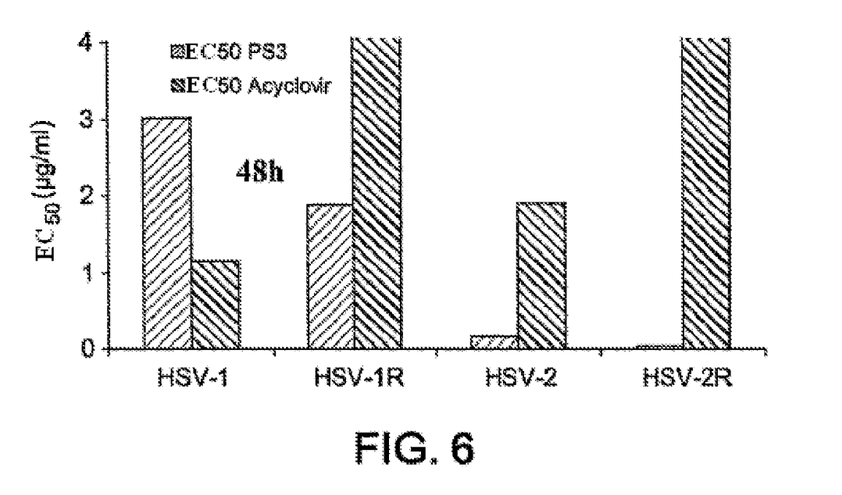
FIG. 6 is a diagram showing the $EC_{50}$ values of PS3 and acyclovir obtained for vero cells infected by the viral suspensions of HSV-1, HSV-1R, HSV-2 and HSV-2R, treated beforehand with PS3 or acyclovir, after culture for 48 hours.
Figure 7:
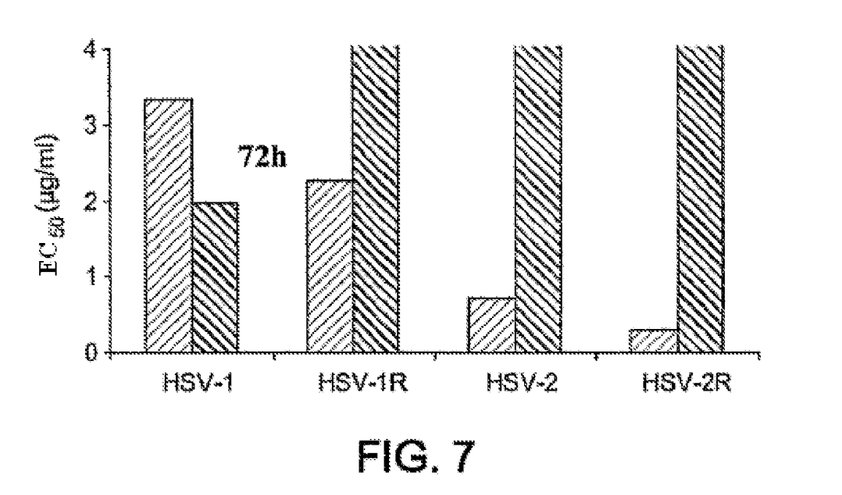
FIG. 7 is a diagram showing the $EC_{50}$ values of PS3 and acyclovir obtained for vero cells infected by the viral suspensions of HSV-1, HSV-1R, HSV-2 and HSV-2R, treated beforehand with PS3 or acyclovir, after culture for 72 hours.
Figure 8A:
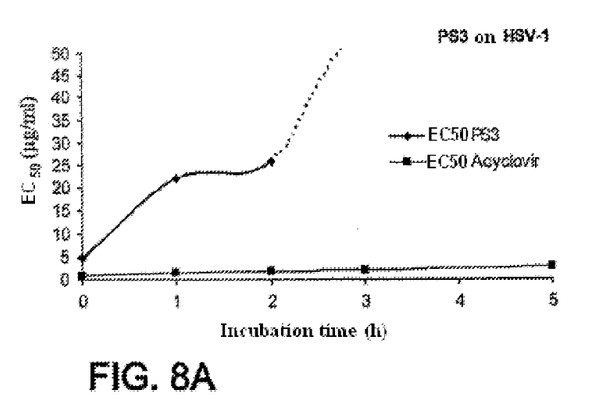
FIG. 8 groups together the four graphs 8A, 8B, 8C and 8D, on which appear the curves representing the course of the $EC_{50}$ values of PS3 and acyclovir as a function of the duration of contact of PS3 or acyclovir with vero cells infected by the viral strains HSV-1 (graph 8A), HSV-1R (graph 8B), HSV-2 (graph 8C) and HSV-2R (graph 8D) respectively.
Figure 8B:
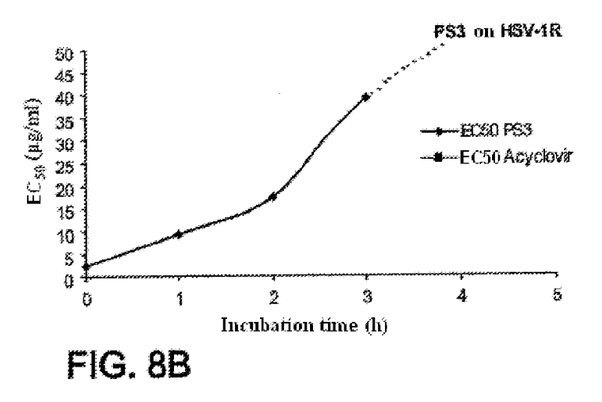
Figure 8C:
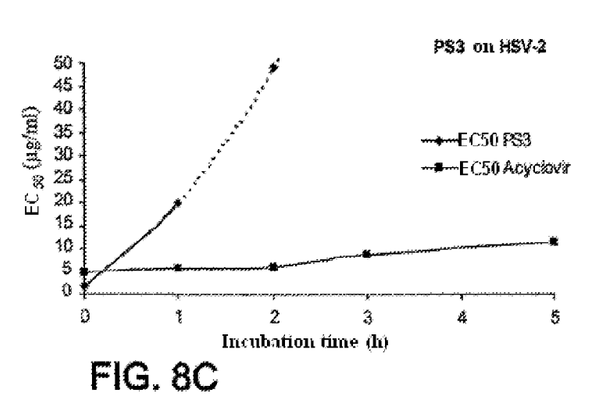
Figure 8D:
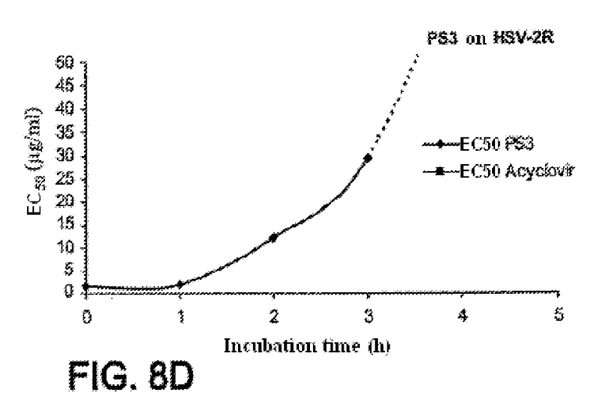
Figure 9A:
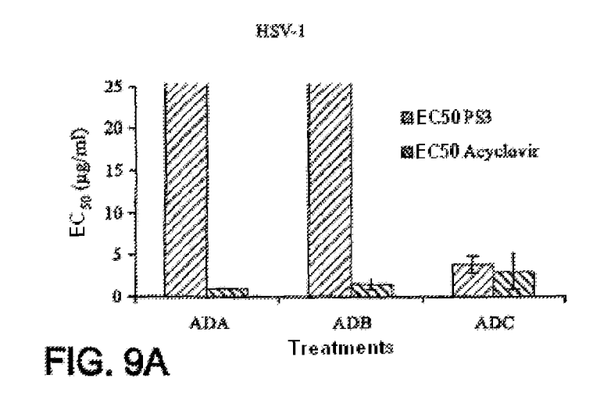
FIG. 9 groups together the four graphs 9A, 9B, 9C and 9D, which demonstrate the effect of PS3 on the viral adsorption of the viral strains HSV-1, HSV-1R, HSV-2 and HSV-2R respectively by measurement of the $EC_{50}$ values of PS3 and acyclovir determined on vero cells treated during infection (treatment A), after infection (treatment B) or during and after infection (treatment C).
Figure 9B:
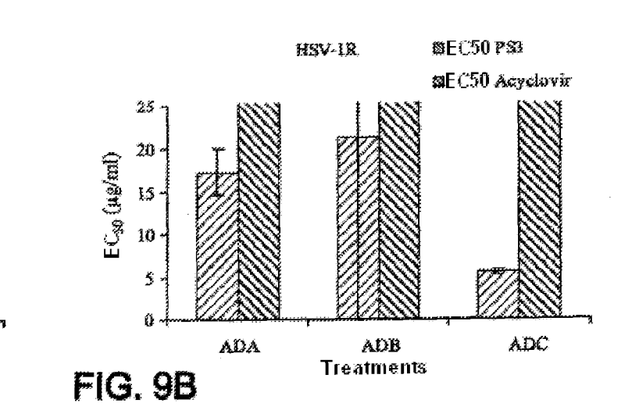
Figure 9C:
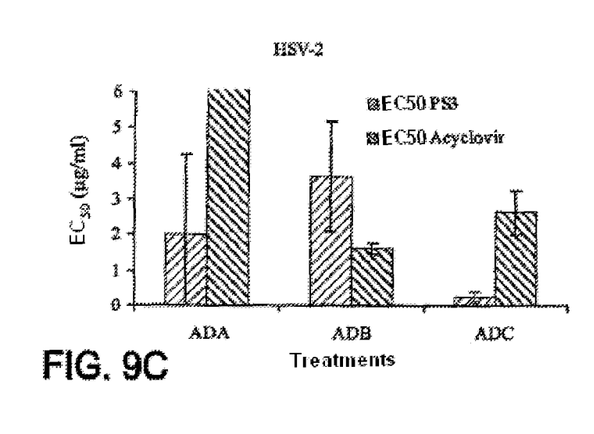
Figure 9D:
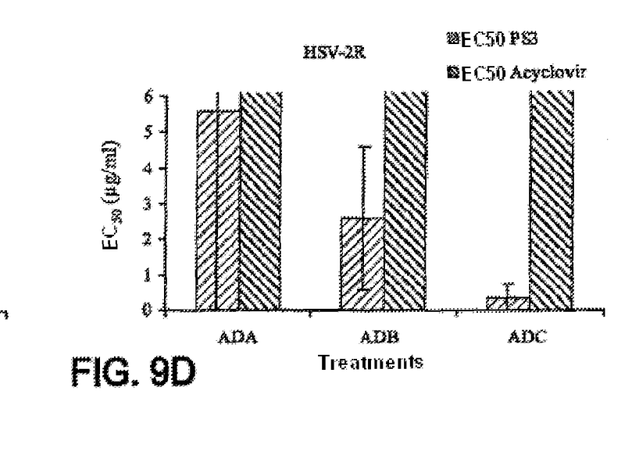

FIGS. 6 and 7 give the $EC_{50}$ of PS3 on the various strains for incubation times of 48 and 72 hours respectively, the comparison product being acyclovir.

If PS3 had a virucidal activity, the $EC_{50}$ values (illustrated by FIGS. 6 and 7) should be lower than those obtained during evaluations of the anti-herpes activity (illustrated by FIGS. 3 and 4). Examination of the results shown in these FIGS. 6 and 7 shows that the $EC_{50}$ values are comparable to those obtained during evaluations of the anti-herpes activity. PS3 therefore has no virucidal effect on the strains studied.

Action of PS3 as a Function of the Moment of its Use

To determine at what moment it is appropriate to use PS3, the procedure was as follows.

Vero cells were seeded at a cell density of $3.5 \cdot 10^4$ cells/well of a 96-well microtitre plate in 100 µl of MEM medium containing 8% FCS and they were then infected by being brought into contact with the various viral strains identified above for 1 hour at 4° C.

The infected cells were then washed with a saline buffer in order to remove the viral particles which had not be adsorbed.

The infected cells were then treated with PS3 or with the comparison product:
either at the moment of infection,
or 1, 2, 3 and 5 hours after infection.

In each case the microtitre plates were kept at 37° C. for 72 hours. The inhibitory effect of PS3 or of the comparison product, in this case acyclovir, was then determined for each viral strain.

FIG. 8 shows the $EC_{50}$ values of PS3 as a function of the moment of bringing PS3 into contact with the cells.

The results demonstrate that PS3 is particularly effective on the viral strains HSV-1R and HSV-2R, even when it is used 3 hours after infection. Acyclovir has no effect on the viral strains HSV-1R and HSV-2R.

Even though the inhibitory effect of PS3 on the four viral strains is confirmed, the results show that the presence of PS3 right at the start of infection enables an effectiveness to be preserved at low concentrations. PS3 is all the more effective when it is introduced early, that is to say right at the start of infection.

Action of PS3 on the Viral Adsorption

To determine whether PS3 has an effect on the viral adsorption, the procedure was as follows.

Vero cells were seeded at a cell density of $3.5 \cdot 10^4$ cells/well of a 96-well microtitre plate in 100 µl of MEM medium containing 8% FCS 24 hours before the test. The viral suspensions of HSV-1, HSV-1R, HSV-2 and HSV-2R, defined by an MOI of 0.01 $ID_{50}$/cell for a cell concentration of 350,000 cells/ml, were tested.

On the day of the test, the cells were subjected to three different treatments designated A, B and C.

According to treatment A, cells treated with 50 µl of PS3 or comparison product (acyclovir) of a given concentration were infected with 50 µl of one of the viral suspensions identified above for one hour at 4° C.

The infected cells were then washed with 100 µl of saline buffer in order to remove the PS3 or the reference product as well as the viral particles which had not been adsorbed by the cells.

After having filled each well with sufficient MEM medium containing 8% FCS to arrive at a volume of 200 µl, the cells were then placed in an oven at 37° C. for 72 hours.

According to treatment B, the cells were brought into contact with one of the viral suspensions identified above for 1 hour at 4° C. The infected cells were then washed with 100 µl of saline buffer in order to remove the viral particles which had not been adsorbed. The cells were then treated for 72 hours with various concentrations of PS3 or reference product in a total volume of 200 µl per well.

According to treatment C, cells treated with 50 µl of PS3 or reference product of a given concentration were infected with 50 µl of one of the viral suspensions identified above for one hour at 4° C. The infected cells were then washed with 100 µl of saline buffer in order to remove the PS3 or the reference product as well as viral particles which had not been adsorbed. The cells were then again brought into contact with various concentrations of PS3 or reference product in a total volume of 200 µl per well for 72 hours.

For these 3 treatments, the inhibitory effect of PS3 and of the reference product (expressed in $EC_{50}$) on the adsorption of the four abovementioned viral strains after 72 hours was evaluated by measurement of the $EC_{50}$ values in accordance with the method described in Example 3.

FIG. 9 shows the $EC_{50}$ of PS3 determined for the four abovementioned viral strains identified above after incubation times of 48 and 72 hours respectively, the comparison product being acyclovir.

Examination of this FIG. 9 shows that the $EC_{50}$ values of PS3 are very low during treatment C, in particular for the strains which have developed a resistance to acyclovir.

In fact, $EC_{50}$ values of PS3 of 3.84 µg/ml are observed for the strain HSV-1, 5.54 µg/ml for the strain HSV-1R, 0.24 µg/ml for the strain HSV-2 and 0.30 µg/ml for the strain HSV-2R.

Consequently, PS3 has an inhibitory effect on the 4 viral strains solely during treatment C, that is to say when PS3 is present at the moment of and after the viral adsorption. PS3 therefore exerts an antiviral activity in the first phase of the viral infection.

Action of PS3 on the Viral Penetration

To determine whether PS3 has an effect on the viral penetration, the procedure was as follows.

Vero cells were seeded at a cell density of $3.5 \cdot 10^4$ cells/well of a microtitre plate in 100 µl of MEM medium containing 8% FCS.

After 24 hours, the confluent cells were brought into contact with 50 µl of a viral suspension for 1 hour at 4° C.

The cell carpet was then incubated with various concentrations of PS3 (0.125-1,250 µg/ml) or reference product, in this case acyclovir (0.005-5 µl/ml), at 37° C. in order to facilitate penetration of the viruses.

After incubation times of 15, 30 and 60 minutes, the corresponding cells were washed with 100 µl of PBS and then treated for 1 minute with 0.5 mg/ml of proteinase K (Sigma) in solution in PBS in order to remove all the extracellular viruses which had not been adsorbed.

This treatment was stopped by addition of 1 mM of phenylmethylsulphonyl fluoride (Sigma) in solution in PBS containing 3% FCS.

The cells were then washed with 100 µl of PBS per well and cultured again at 37° C. in 200 µl of MEM medium supplemented with 8% FCS.

Controls of the growth of the cells and of the viruses were run simultaneously. After incubation for 48 hours, the effect of PS3 and of acyclovir on the penetration of the virus was measured using the neutral red method.

The results obtained demonstrate that PS3 has no antiviral activity on penetration of the virus into the cell in the case of the four viral strains.

The results obtained in the experiments just described in relation to the four viral strains identified above are shown in Table (II).

TABLE II

|  | PS3<br>Viral strains studied:<br>HSV-1, HSV-2, HSV-1R,<br>HSV-2R | Acyclovir<br>Non-resistant strains<br>HSV-1 and HSV-2 |
|---|---|---|
| Effect before infection | no | no |
| Virucidal effect | no | no |
| Effect in relation to the moment of addition | not very effective after infection | effective up to 5 hours after infection |
| Effect on adsorption | yes | no |
| Effect on penetration | no | no |

In conclusion, PS3 has an antiviral activity with regard to the four viral strains tested, HSV-1, HSV-1R, HSV-2, HSV-2R, acting more particularly on the adsorption of the viruses on the cells; it is effective when present from the start of the infection.

It is particularly important to underline that PS3 has an anti-herpes effect with regard to viral strains resistant to acyclovir.

The invention therefore quite particularly provides the use of PS3 for the preparation of a medicament for a treatment against herpes virus strains resistant to inhibitors of the nucleoside analogue type, and in particular to acyclovir.

In immunocompetent individuals, the development of a herpes infection caused by strains of virus resistant to acyclovir is very rare.

In contrast, in the case of immunodeficient individuals, this risk of developing herpes infections caused by strains resistant to nucleoside analogues is greater.

Immunodeficient individuals are those who are undergoing an immunodepressant therapy, those who have received an organ transplant, as well as those suffering from acquired immunodeficiency syndrome (AIDS), or also those who have major changes to the skin, such as major burns.

EXAMPLE 8

Measurement of the In Vivo Toxicity of the Sulphated Laminarin PS3

A possible in vivo toxicity of the sulphated laminarin PS3 used according to the invention was also investigated.

This study was carried out on white rabbits of the New Zealand breed and on rats of the Sprague Dawley breed.

The white rabbits were subjected on the one hand to the ocular irritation test and on the other hand to the primary skin irritation test.

As the outcome of the first of these tests, a slightly irritating action was concluded, and in the second a non-irritating action was concluded.

The rats were subjected on the one hand to a study for determination of the acute dermal toxicity and on the other hand to a study for determination of the acute oral toxicity.

In the first case the dermal 50% lethal dose is greater than 2 g/kg of body weight, which makes it possible to affirm that the product is not toxic.

In the second case the acute toxicity by the oral route can be considered to be greater than 2 g/kg of body weight, which again allows classification of the product as non-toxic.

EXAMPLE 9

Measurement of the Anticoagulant Activity of the Sulphated Laminarin PS3

It has been shown that the anticoagulant activity of the sulphated laminarin PS3 is low enough, compared with that of heparin, not to constitute a drawback in the context of the use according to the invention, and that it is not cytotoxic at the highest concentrations which may be used.

For this, the anticoagulant activity of the laminarin sulphate PS3 obtained in Example 1 was determined as a function of its concentration in comparison with that of heparin in the conventional coagulation, APTT or "activated partial thromboplastin time" tests, the prothombin time test, the so-called "HEPTEST" test and the thrombin time test. The APTT reflects an interaction with the intrinsic coagulation system, while the prothrombin time reflects an interaction with the extrinsic coagulation; the so-called "HEPTEST" test is the conventional test for measurement of the inhibitory activity of heparin with respect to factor Xa, and the thrombin time corresponds to the last stage of coagulation, that is to say the formation of fibrins induced by thrombin. It has been possible to demonstrate that, in contrast to that of heparin, the activity of the laminarin sulphate PS3 in the so-called "HEPTEST" test is more than 20 times weaker. Similarly, in relation to the prothrombin time, the laminarin sulphate PS3 showed no pronounced anticoagulant effect as in the case of heparin. The specific activity (IU/mg) in the APTT represents 30% of the heparin activity, and in the case of the thrombin time 60%. To prevent coagulation totally, it was necessary to apply a concentration 4 times higher in the case of the APTT and a concentration 20 times higher in the case of the thrombin time.

In the specific anti-factor Xa and antithrombin tests using chromogenic substrates, it was found that the laminarin sulphate PS3, in contrast to heparin, has neither a significant anti-factor Xa activity dependent on the antithrombin nor an antithrombin activity. The effect in the case of the thrombin time can be considered as being due to an inhibition of thrombin dependent on heparin cofactor II. On the basis of on the one hand the lower specific activity and on the other hand the profile dependent on the concentration and also on the other hand other investigations relating to the action mechanism, it is possible to consider that in the case of the laminarin sulphate PS3, the risk of bleeding is considerably lower than in the case of heparin.

It follows that the anti-herpes properties of the laminarin sulphate PS3 could advantageously be put to good use without fearing undesirable secondary effects on coagulation.

The experiments which have allowed these conclusions to be arrived at were carried out under the direction of Dr. SHRIVASTAVA in the Toxicology Department of the establishment called Elevage Scientifique des Dombes (ESD)

Romans

01400 Chatillon Sur Chalaronne observing the OECD Guidelines no. 404 and 405 of 24 Feb. 1987 to the extent that they are studies carried out on white rabbits, and OECD Guidelines no. 401 and 402 (1987) as well as EEC Directive B-I 92/69 (1992) to the extent that they are studies carried out on Sprague Dawley rats.

The sulphated laminarin tested originated from PS3 batch 8/2001 provided by Laboratoires Goëmar.

The corresponding reports are stored in the archives of the applicant company.

EXAMPLE 10

Composition of a Cream Based on Sulphated Laminarin PS3

A cream based on sulphated laminarin PS3 having the following composition was produced:

| | |
|---|---|
| Demineralized water | 69.7% |
| Glycerin | 5.0% |
| Sulphated laminarin PS3 | 1.0% |
| PEG 100 stearate | 4.0% |
| Cetearyl alcohol | 2.0% |
| Preservative | 1.0% |
| PEG 40 stearate | 3.0% |
| Vitamin E acetate | 0.5% |
| $C_{12-15}$-alkyl benzoate | 6.5% |
| Caprylic/capric triglycerides | 5.5% |
| NaOH 0.1 N | 1.8% |
| | 100% |

It is possible to envisage 2 to 5 applications per day.

EXAMPLE 11

Composition of a Solution for Aerosol Based on Sulphated Laminarin PS3

A solution for aerosol based on sulphated laminarin PS3 having the following composition was produced:

| | |
|---|---|
| Sulphated laminarin PS3 | 2.5% |
| Sodium chloride | 9.0% |
| Demineralized water European Pharmacopoeia | 88.5% |

It is possible to administer an amount of aerosol corresponding to an amount of 1,000 to 10,000 μg of active ingredient daily.

EXAMPLE 12

Composition of a Suppository Based on a Potassium Sulphate Salt of oligo-β-1-3-glucan A suppository based on a potassium sulphate salt of oligo-β-1-3-glucan having the following composition was produced:

| | |
|---|---|
| Potassium sulphate salt of oligo-β-1-3-glucan (DP = 22, degree of sulphation (DS) of 2.4) | 5.0% |
| Solid semi-synthetic glycerins | 95.0% |

Administration 1 or 2 times per day is recommended.

EXAMPLE 13

Composition of an Injectable Solution Based on an Oligolaminaritol Sulphate Sodium Salt An injectable solution based on an oligolaminaritol sulphate sodium salt having the following composition was produced:

| | |
|---|---|
| Oligolaminaritol sulphate sodium salt (DP 20, DS 2.3) | 5.0% |
| Sodium bicarbonate | 3.0% |
| Water for injectable preparations | 92.0% |

Over a period of 24 hours it is possible to administer from 1,000 to 3,000 ml of the injectable solution.

EXAMPLE 14

Composition of a Vaginal Solution Based on an oligo-β-1-3-glucan Sulphate Sodium Salt

A vaginal solution based on an oligo-O-1-3-glucan sulphate sodium salt in the form of a unidose bottle of 140 ml with a cannula and having the following composition was realised:

| | |
|---|---|
| Oligo-β-1-3-glucan sulphate sodium salt (DP 23, DS 2.4) | 0.1% |
| Sodium chloride | 9.0% |
| 95% Ethyl alcohol | 5.0%, |
| Rose fragrance | 0.2% |
| Purified water | 84.7% |
| Preservatives (benzalkonium chloride) | 0.2% |
| Sodium edetate | 0.3% |
| Polysorbate 20 | 0.5% |
| | 100% |

It is possible to apply the composition one or two times per day.

The invention claimed is:

1. A method for treating a disease caused by a herpes virus, wherein the method comprises administrating to a patient suffering from said disease caused by a herpes virus an effective amount of a polysaccharide of formula (I)

wherein
$R^1$ represents either a hydrogen atom, a sulphate group, or a sulphated glucose bonded to the saccharide structure,
$R^2$ represents a hydrogen atom, a sulphate group, provided that $R^1$ and $R^2$ are not both hydrogen atoms simultaneously,
X and Y each independently represent an OH group, a glucose, a sulphated glucose, a mannitol or a sulphated mannitol,
n represents an integer from 11 to 30,
said polysaccharide having a degree of sulphation greater than 2.

2. The method for treating a disease caused by a herpes virus according to claim 1, wherein the polysaccharide of formula (I) is a sulphated laminarin having a degree of sulphation greater than 2 and a degree of polymerization of 11 to 28.

3. The method for treating a disease caused by a herpes virus according to claim 1, wherein said method further comprises a simultaneous, separate or sequential administration of an effective amount of at least one compound selected from the group consisting of nucleoside inhibitors and non-nucleoside inhibitors of a viral enzyme of a herpes virus.

4. The method for treating a disease caused by a herpes virus according to claim 1, wherein said patient suffering from the disease caused by a herpes virus is an immunodeficient individual.

5. The method for treating a disease caused by a herpes virus according to claim 1, wherein said disease is caused by an alpha-herpes virus.

6. The method for treating a disease caused by a herpes virus according to claim 1, wherein said disease is caused by a herpes virus selected from the group consisting of HSV-1 and HSV-2.

7. The method for treating a disease caused by a herpes virus according to claim 1, wherein said disease is caused by a strain of a alpha-herpes virus which is resistant to the antiviral agents known to date.

8. The method for treating a disease caused by a herpes virus according to claim 1, wherein the R1 moiety of the polysaccharide of formula (I) represents either a hydrogen atom, a sulphate group, or a sulphated glucose bonded to the saccharide structure by a bond of the $\beta(1 \to 6)$ type.

9. The method for treating a disease caused by a herpes virus according to claim 3, wherein the nucleoside inhibitors of a viral enzyme of a herpes virus are selected from the group consisting of acyclovir, penciclovir, cidofovir, ganciclovir, valganciclovir, valacyclovir and famciclovir.

10. The method for treating a disease caused by a herpes virus according to claim 3, wherein the non-nucleoside inhibitors of a viral enzyme of a herpes virus are selected from the group consisting of analogues of inorganic pyrophosphate.

11. The method for treating a disease caused by a herpes virus according to claim 3, wherein the non-nucleoside inhibitor of a viral enzyme of a herpes virus is foscarnet.

12. The method for treating a disease caused by a herpes virus according to claim 4, wherein said patient suffering from a disease caused by a herpes virus is selected from the group consisting of individuals who have received transplants, individuals suffering from acquired immunodeficiency syndrome and individuals who have major changes to the skin.

13. The method for treating a disease caused by a herpes virus according to claim 4, wherein said patient suffering from a disease caused by a herpes virus is a major burned individual.

14. A method for treating a disease caused by a herpes virus, wherein the method comprises administering to a patient suffering from said disease caused by a herpes virus an effective amount of sulphated laminarin having a degree of sulphation of 2.3 and a degree of polymerization of 23 to 28.

* * * * *